(12) United States Patent
Codella et al.

(10) Patent No.: US 9,652,846 B1
(45) Date of Patent: May 16, 2017

(54) VIEWPOINT RECOGNITION IN COMPUTER TOMOGRAPHY IMAGES

(71) Applicant: INTERNATIONAL BUSINESS MACHINES CORPORATION, Armonk, NY (US)

(72) Inventors: Noel Codella, Yorktown Heights, NY (US); Mehdi Moradi, San Jose, CA (US); Tanveer Syeda-Mahmood, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 22 days.

(21) Appl. No.: 14/920,604

(22) Filed: Oct. 22, 2015

(51) Int. Cl.
| | |
|---|---|
| *G06K 9/00* | (2006.01) |
| *G06T 7/00* | (2017.01) |
| *G06K 9/62* | (2006.01) |
| *A61B 6/03* | (2006.01) |
| *A61B 6/00* | (2006.01) |

(52) U.S. Cl.
CPC ............ *G06T 7/0012* (2013.01); *A61B 6/032* (2013.01); *A61B 6/503* (2013.01); *G06K 9/6267* (2013.01); *G06T 7/0081* (2013.01); *G06T 2207/10081* (2013.01); *G06T 2207/30048* (2013.01)

(58) Field of Classification Search
None
See application file for complete search history.

(56) References Cited

U.S. PATENT DOCUMENTS

| | | | |
|---|---|---|---|
| 8,023,710 B2 | 9/2011 | Summers et al. | |
| 8,355,553 B2* | 1/2013 | Fidrich | G06T 7/149 382/131 |
| 8,712,120 B1* | 4/2014 | Reicher | H04L 67/02 382/128 |
| 8,917,917 B2 | 12/2014 | Beymer et al. | |
| 2005/0228250 A1* | 10/2005 | Bitter | A61B 5/02007 600/407 |

(Continued)

FOREIGN PATENT DOCUMENTS

WO    2009066053    5/2009

OTHER PUBLICATIONS

Deepa et al., "A survey on artificial intelligence approaches for medical image classification," Indian Journal of Science and Technology, Nov. 2011, 4(11), pp. 1583-1595.
(Continued)

*Primary Examiner* — Shervin Nakhjavan
(74) *Attorney, Agent, or Firm* — IP Authority, LLC; Ramraj Soundararajan

(57) ABSTRACT

A solution is presented for cardiac CT viewpoint recognition to identify the desired images for a specific view and subsequent processing and anatomy recognition. A new set of features is presented to describe the global binary pattern of cardiac CT images characterized by the highly attenuating components of the anatomy in the image. Five classic image texture and edge feature sets are used to devise a classification approach based on SVM classification, class likelihood estimation, and majority voting, to classify 2D cardiac CT images into one of six viewpoint categories that include axial, sagittal, coronal, two chamber, four chamber, and short axis views. Such an approach results in an accuracy of 99.4% in correct labeling of the viewpoints.

24 Claims, 5 Drawing Sheets

(56) References Cited

U.S. PATENT DOCUMENTS

| | | | |
|---|---|---|---|
| 2007/0165924 A1* | 7/2007 | Nicponski | G06T 7/0012 382/128 |
| 2008/0234571 A1* | 9/2008 | Hay | A61B 6/032 600/425 |
| 2008/0267471 A1* | 10/2008 | Yu | G06K 9/4604 382/128 |
| 2009/0175531 A1 | 7/2009 | Boroczky et al. | |
| 2010/0061609 A1* | 3/2010 | Shinagawa | G06K 9/6212 382/131 |
| 2010/0329521 A1 | 12/2010 | Beymer et al. | |
| 2011/0206240 A1* | 8/2011 | Hong | G06K 9/00771 382/103 |
| 2011/0206250 A1* | 8/2011 | McGinnis | G06T 7/0012 382/128 |
| 2012/0207359 A1 | 8/2012 | Konukoglu et al. | |
| 2013/0094749 A1* | 4/2013 | Oh | A61B 6/503 382/133 |
| 2013/0315457 A1 | 11/2013 | Beymer et al. | |
| 2014/0172643 A1* | 6/2014 | Fazl Ersi | G06K 9/4642 705/26.64 |
| 2015/0148677 A1* | 5/2015 | Mullick | A61B 8/5223 600/443 |
| 2015/0379709 A1* | 12/2015 | Liang | G06T 7/0012 382/131 |
| 2016/0015347 A1* | 1/2016 | Bregman-Amitai | G06T 7/0012 382/131 |
| 2016/0331224 A1* | 11/2016 | Uji | A61B 3/0025 |

OTHER PUBLICATIONS

Yalamanchili et al., "Knowledge-based Quantification of Pericardial Fat in Non-Contrast CT Data," Proceedings of SPIE, Mar. 2010, V7623, 8pgs.

Xie, Hongmei, "Medical CT Image Classification," CT Scanning—Techniques and Applications, Oct. 2011, <http://intechopen.com/books/ct-scanning-techniques-and-applications/medical-ct-image-classification>, 15pgs.

Rahman et al., "Medical Image Retrieval with Probabilistic Multi-Class Support Vector Machine Classifiers and Adaptive Similarity Fusion," Computerized Medical Imaging and Graphics, Mar. 2008, 32(2), pp. 95-108.

Padma et al., "Automatic Classification and Segmentation of Brain Tumor in CT Images using Optimal Dominant Gray level Run length Texture Features," Int'l Journal of Advanced Computer Science and Applications, 2(10), 2011, pp. 53-59.

Park et al., "Automatic Cardiac View Classification of Echocardiogram," ICCV 2007, Oct. 14-21, 2007, Rio de Janeiro, 8pgs.

Kumar et al., "Echocardiogram View Classification Using Edge Filtered Scale-Invariant Motion Features," IEEE Conf on Computer Vision and Pattern Recognition, CVPR 2009, Miami, Florida, USA, Jun. 20-25, 2009, pp. 723-730.

Syeda-Mahmood et al., "AALIM: Mutimodal Mining for Cardiac Decision Support," Computers in Cardiology, 2007, V34, pp. 209-212.

Budoff et al., "Assessment of Coronary Artery Disease by Cardiac Computed Tomography," Circulation, V114, 2006, pp. 1761-1791.

Gueld et al., "Quality of DICOM Header Information for Image Categorization," Proc. SPIE 4685, Medical Imaging 2002: PACS and Integrated Medical Information Systems: Design and Evaluation, May 16, 2002, 8pgs.

Yoshimura et al., "Operating Data and Unsolved Problems of the DICOM Modality Worklist: An Indispensable Tool in an Electronic Archiving Environment," Radiation Medicine, 21(2), 2003, pp. 68-73.

Top et al., "Active Learning for Interactive 3D Image Segmentation," Medical Image Computing and Computer-Assisted Intervention (MICCAI), V6893 of LNCS, Springer Berlin / Heidelberg, 2011, pp. 603-610.

Cao et al., IBM Research and Columbia University TRECVID—2013 Multimedia Event Detection (MED), Multimedia Event Recounting (MER), Surveillance Event Detection (SED), and Semantic Indexing (SIN) Systems, NIST TRECVID Workshop, 2012, 18pgs.

Ojala et al., "A Comparative Study of Texture Measures with Classification Based on Featured Distributions," Pattern Recognition, 29(1), 1996, pp. 51-59.

Liao et al., "A Fast Algorithm for Multilevel Thresholding," Journal of Information Science and Engineering, V17, 2001, pp. 713-727.

Platt, Probabilistic Outputs for Support Vector Machines and Comparisons to Regularized Likeihood Methods, Advances in Large Margin Classifiers, 10(3), 1999, pp. 61-74.

Krizhevsky et al., "Imagenet Classification with Deep Convolutional Neural Networks," Proceedings of Neural Information Processing Systems (NIPS), 2012, 9pgs.

Codella et al., "Automated Medical Image Modality Recognition by Fusion of Visual and Text Information," MICCAI, V8674 of LNCS, 2014, pp. 487-495.

Caruana et al., "Ensemble Selection from Libraries of Models," ICML 2004 Proceedings of the 21st International Conf. on Machine Learning, New York, NY, USA, 2004, 9pgs.

* cited by examiner

VIEWPOINT RECOGNITION IN COMPUTER TOMOGRAPHY IMAGES

BACKGROUND OF THE INVENTION

Field of Invention

The present invention relates generally to the field of computed tomography (CT). More specifically, the present invention is related to view point recognition in CT images.

Discussion of Related Art

Coronary heart disease is the most common cause of mortality in the United States and contributes to one in every five deaths, according to the American Heart Association. Acute coronary symptoms result in hospitalization of nearly 900,000 Americans every year. Cardiac catheterization under CT or X-ray angiography provides definitive evidence for plaque build-up in coronary arteries. However, the invasive nature of such procedures prohibits their use for screening purposes in low to intermediate risk individuals. This has created a growing interest in cardiac computed tomography (CT) as an imaging technology to study the heart vessels and chambers for screening purposes. Several studies have shown that cardiac CT, without the use of a contrast agent, has a very high specificity and provides a negative predictive value of nearly 100% and can be used to rule out a large number of low and intermediate risk patients without the need for invasive methods (see for example, the paper to Budoff et al. titled "Assessment of Coronary Artery Disease by Cardiac Computed Tomography," Circulation 114, 2006, pp. 1761-1791).

The effective and wide-spread use of CT as a screening methodology for cardiovascular disease could be facilitated by the introduction of an end-to-end cardiology/radiology "cognitive assistant". A cognitive assistant is a software system with the ability to automatically complete the pre-processing steps, recognize or generate the appropriate views within a complete scan, extract relevant features and concepts from an image and the text associated with the image, run image analysis methods to extract relevant features, and generate a clinically relevant outcome, such as the calcium score or likelihood of disease. These kinds of systems have the ability to reduce the workload, prevent errors, and enable population screening. As an example, previous work (see, for example, the paper to Syeda-Mahmood et al. titled "Aalim: Multimodal Mining for Cardiac Decision Support," Computers in Cardiology, vol 34, 2007, pp. 209-212) has reported a decision support system for cardiology that derives the consensus opinions of other physicians who have looked at similar cases. Such a decision support system generates a report that summarizes possible diagnoses based on statistics from similar cases. In deploying a system of this type, one needs to retrieve the relevant or similar images and activate the image analytics processes that are often dependent on the modality and viewpoint of the image.

In cardiac imaging, the viewpoint of the image is an essential input for any algorithm designed to measure clinical features of the heart, such as detection of left ventricle, valves, thickness of the pericardium, etc. Since viewpoint recognition is often the first step in the analytic pipeline within a cognitive assistant system, a nearly perfect classification accuracy is needed. Even though DICOM headers (based on the Digital Imaging and Communications in Medicine standard) provide optional tags to store modality information, viewpoint is often not recorded. Also, as several investigators have reported (see, for example, the paper to Gueld et al. titled "Quality of DICOM Header Information for Image Categorization," SPIE Medical Imaging, vol. Proc. SPIE 4685, 2002, pp. 280-287), one cannot rely on the accuracy and completeness of DICOM headers for image categorization particularly on optional and manually entered tags (see, for example, the paper to Yoshimura et al. titled "Operating Data and Unsolved Problems of the DICOM Modality Worklist: An Indispensable Tool in an Electronic Archiving Environment," Radiation Medicin, v21(2), 2003, pp. 68-73). The introduction of a machine learning approach to slice/viewpoint recognition could also facilitate the use of 2D technics in segmentation and anatomy recognition within the cognitive assistant system, providing savings in terms of computational resources compared to 3D.

Much of the previous work in cardiac viewpoint detection focuses on echocardiography images (see, for example, the paper to Park et al. titled "Automatic Cardiac View Classification of Echocardiogram," ICCV, 2007, pp. 1-8, and the paper to Kumar et al. titled "Echocardiogram View Classification Using Edge Filtered Scale-Invariant Motion Features," IEEE CVPR, 2009, pp. 723-730). Due to the small field of view, the free-hand nature of ultrasound images, and the fundamentally different nature of ultrasound image texture, the methods cannot be directly applied to CT imaging.

Embodiments of the present invention are an improvement over prior art systems and methods.

SUMMARY OF THE INVENTION

The present invention remedies the above-mentioned problems with the prior art by providing a solution to the problem of viewpoint recognition in cardiac CT images. The utility of a number of different types of texture and edge characterizing features are explored for the purpose of image classification. A new set of features are proposed that rely on the anatomic context of the CT images, particularly a set of features that rely on the pattern of the appearance of bone structures of the rib cage and the vertebral column, where the new set of features provide a solution for global binary characterization of cardiac images. The image classification features are combined with the global binary pattern features in an innovative machine learning framework based on support vector machine classification and voting to determine the correct image viewpoint from six different viewpoints. The present invention's solution provides accurate performance in cardiac CT viewpoint recognition.

The present invention in one embodiment provides a system for computed tomography (CT) viewpoint recognition in CT images comprising: a feature engine comprising a global binary pattern feature calculation unit and at least one image feature calculation unit, the global binary pattern feature calculation unit: preprocessing the CT images with histogram equalization to maximize contrast in one or more pre-determined regions, applying Otsu thresholding to the preprocessed CT images and extracting connected components, and forming a feature vector based on the extracted connected components; a cognitive engine comprising a plurality of classifiers (e.g., support vector machine (SVM) classifiers), one for each of the global binary calculation unit and at least one image feature calculation unit; a voting unit picking a class label for each of the CT images based on a majority voting scheme determining the most frequently returned label among the classifiers.

The present invention in another embodiment provides a system for computed tomography (CT) viewpoint recognition in CT images comprising: a feature engine comprising: one or more image feature calculation units picked from the following: statistical image texture feature calculation unit, curvelet feature calculation unit, wavelet feature calculation unit, edge histogram features calculation unit, and local binary pattern (LBP) features calculation unit; a global binary pattern feature calculation unit: preprocessing the CT images with histogram equalization to maximize contrast in one or more pre-determined regions, applying Otsu thresholding to the preprocessed CT images and extracting connected components, and forming a feature vector based on the extracted connected components; a cognitive engine comprising a plurality of classifiers (e.g., SVM classifiers), one for each of the global binary calculation unit and each of the image feature calculation units; and a voting unit picking a class label for each of the CT images based on a majority voting scheme determining the most frequently returned label among the classifiers.

The present invention in another embodiment provides a method for computed tomography (CT) viewpoint recognition in CT images comprising: preprocessing the CT images with histogram equalization to maximize contrast in one or more pre-determined regions; applying Otsu thresholding to the preprocessed CT images and extracting connected components; forming a feature vector based on the extracted connected components; applying a plurality of classifiers (e.g., SVM classifiers), one for the feature vector formed from extracted connected components and one for each calculated image feature; and picking a class label for each of the CT images based on a majority voting scheme determining the most frequently returned label among the classifiers.

The present invention in another embodiment provides an article of manufacture having non-transitory computer readable storage medium comprising computer readable program code executable by a processor to implement a method for computed tomography (CT) viewpoint recognition in CT images, the non-transitory computer readable storage medium comprising: computer readable program code preprocessing the CT images with histogram equalization to maximize contrast in one or more pre-determined regions; computer readable program code applying Otsu thresholding to the preprocessed CT images and extracting connected components, computer readable program code forming a feature vector based on the extracted connected components; computer readable program code applying a plurality of classifiers (e.g., SVM), one for the feature vector formed from extracted connected components and one for each calculated image feature; and computer readable program code picking a class label for each of the CT images based on a majority voting scheme determining the most frequently returned label among the classifiers.

The present invention, in another embodiment, provides a method for use with a 3-D computed tomography (CT) image of anatomy relevant to a medical condition, wherein the method comprising: generating a binary image of the CT image, the binary image delineating bone from soft tissue; analyzing the binary image with a machine learning component to train a classifier within the machine learning component and generating a taxonomy related to anatomical viewpoints of the CT image; ranking a plurality of 2-D slices of the CT image based on the generated taxonomy; and selecting a 2-D slice among the plurality of 2-D slices that is most relevant to the medical condition based on the ranking.

BRIEF DESCRIPTION OF THE DRAWINGS

The present disclosure, in accordance with one or more various examples, is described in detail with reference to the following figures. The drawings are provided for purposes of illustration only and merely depict examples of the disclosure. These drawings are provided to facilitate the reader's understanding of the disclosure and should not be considered limiting of the breadth, scope, or applicability of the disclosure. It should be noted that for clarity and ease of illustration these drawings are not necessarily made to scale.

FIG. 2A is the axial view, FIG. 2B is the sagittal view, and FIG. 2C is the coronal view.

FIG. 2D is the four chamber (4C) view, FIG. 2E is the short axis (SHA) view, and FIG. 2F is the two chamber (2C) view.

DESCRIPTION OF THE PREFERRED EMBODIMENTS

Figure 1:
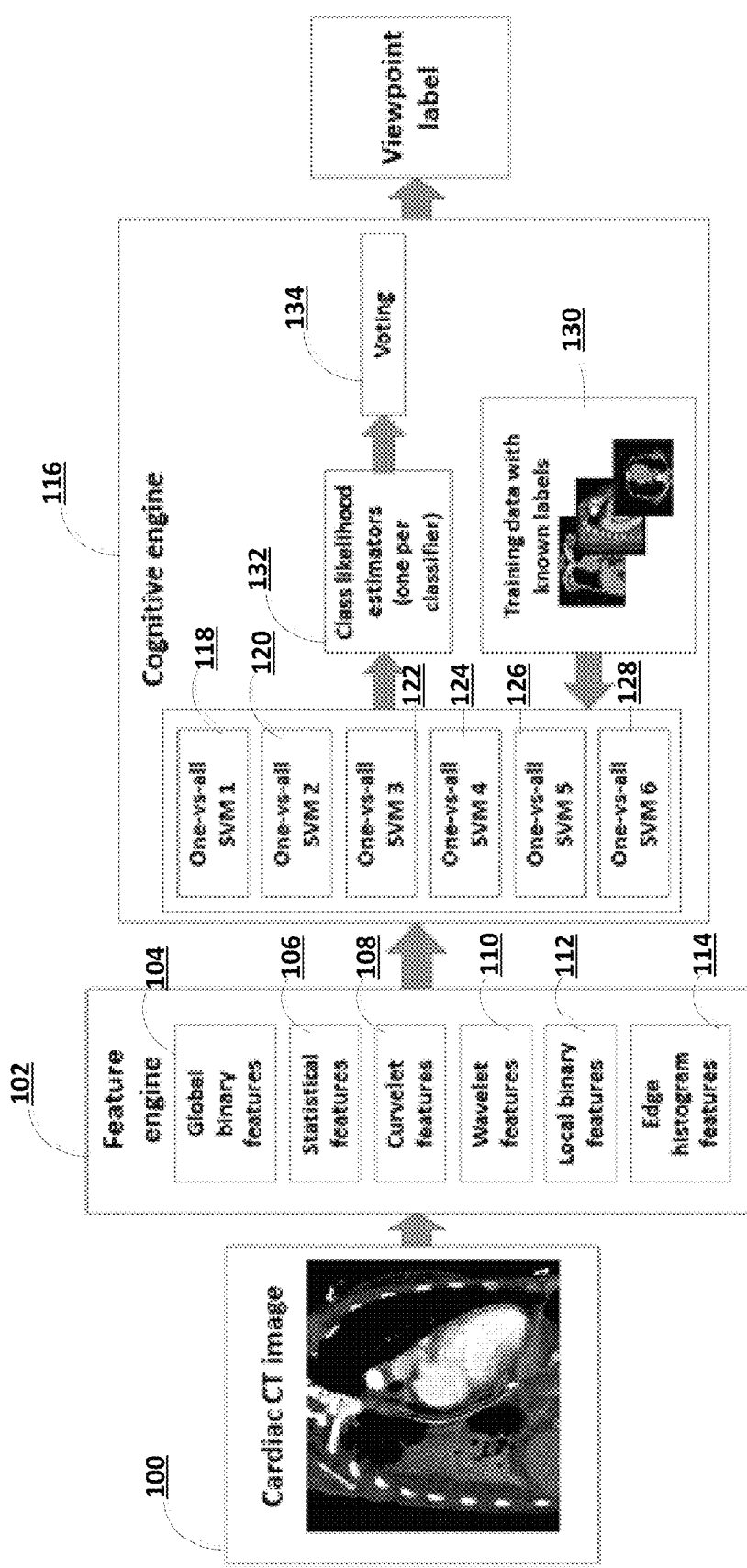
FIG. 1 illustrates a block diagram of the present invention's cardiac CT viewpoint recognition system.

While this invention is illustrated and described in a preferred embodiment, the invention may be produced in many different configurations. There is depicted in the drawings, and will herein be described in detail, a preferred embodiment of the invention, with the understanding that the present disclosure is to be considered as an exemplification of the principles of the invention and the associated functional specifications for its construction and is not intended to limit the invention to the embodiment illustrated. Those skilled in the art will envision many other possible variations within the scope of the present invention.

Note that in this description, references to "one embodiment" or "an embodiment" mean that the feature being referred to is included in at least one embodiment of the invention. Further, separate references to "one embodiment" in this description do not necessarily refer to the same embodiment; however, neither are such embodiments mutually exclusive, unless so stated and except as will be readily apparent to those of ordinary skill in the art. Thus, the present invention can include any variety of combinations and/or integrations of the embodiments described herein.

The Data and the Classes

The most common protocol for cardiac CT is multi-slice imaging with a minimum of 64 axial slices. Volumetric re-sampling is performed to obtain any arbitrary plane. Most commonly, clinicians use the three standard orthogonal planes that are parallel to the cardinal planes. As such, a viewpoint recognition system for CT imaging should correctly label sagittal, axial and coronal planes. There are also oblique planes that are obtained to assess cardiac chamber morphology, size and function. Short axis view (SHA) through the entire left ventricle is useful in calculation of left ventricle volume and ejection fraction, whereas the function of the left ventricle should be reviewed in long axis views which include the two chamber (2C) and four chamber (4C) views. There are also three chamber and five chamber views that are useful to study the aortic valve and left ventricle outflow. However, these two views may be generated with the maximum intensity projection technic as opposed to re-sampling.

The effectiveness of the present invention is studied with respect to three different viewpoint recognition problems:

classification of standard orthogonal planes (axial/sagittal/coronal), classification of the most commonly used re-sampled non-cardinal views (SHA, 2C, 4C), and a six-class classification problem that includes both the cardinal and non-cardinal planes.

FIG. 1 illustrates a block diagram of the present invention's cardiac CT viewpoint recognition system. It is also important to note that each of these three non-cardinal planes are fairly close to one of the cardinal planes (4C to axial, 2C to coronal and SHA to sagittal). The embodiment shown in FIG. 1 comprises: a feature engine 102 that calculates several groups of image features characteristic of texture and content of input images 100 and a cognitive engine 116 comprising a plurality of classifiers 118 through 128, each receiving the output of the feature engine. The classifiers are trained using data with known viewpoint labels. In one embodiment, within the feature engine 102, there are six feature calculation units (i.e., global binary features calculation unit 104, statistical features calculation unit 106, curvelet features calculation unit 108, wavelet features calculation unit 110, local binary features calculation unit 112, and edge histogram features calculation unit 114) each calculating a groups of features.

Each test image is used as an input to the feature engine and then the feature values are used as inputs to the classifiers in the cognitive engine. Each classifier produces a label and the final image label is generated based on a majority vote between the classifiers.

As a non-limiting example, data used in this description consist of cardiac CT data obtained in standard axial planes, with 2 mm slice thickness. The open source software package TurtleSeg (see paper to Top et al. titled "Active Learning for Interactive 3D Image Segmentation," Medical Image Computing and Computer-Assisted Intervention (MICCAI), vol 6893 of LNCS, Springer Berlin/Heidelberg, 2011, pp. 603-610) was used to re-sample the sagittal images, coronal images and the 2C, 4C, & SHA oblique views, which were then examined and confirmed by an experienced radiologist. A total of 168 images, equally distributed between the six viewpoint types were used, which were from 28 contrast-enhanced 3D scans, each from a different patient.

Figure 2A:
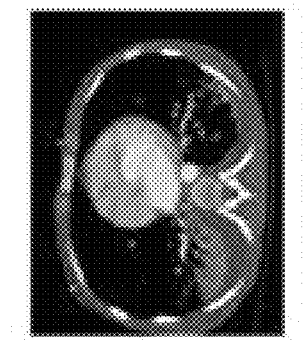
FIGS. 2A-C illustrate standard cardinal views associated with cardiac CT images, where
Figure 2B:
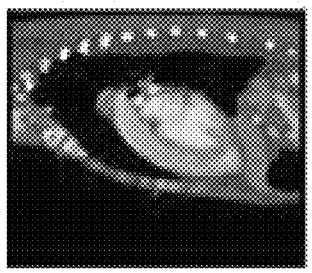
Figure 2C:
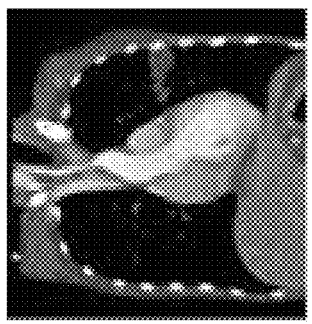
Figure 2D:
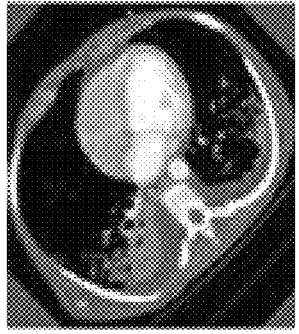
FIGS. 2D-F illustrate non-cardinal views associated with cardiac CT images, where
Figure 2E:
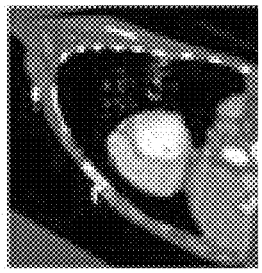
Figure 2F:

FIGS. 2A-C illustrate standard cardinal views associated with cardiac CT images, where FIG. 2A is the axial view, FIG. 2B is the sagittal view, and FIG. 2C is the coronal view. FIGS. 2D-F illustrate non-cardinal views associated with cardiac CT images, where FIG. 2D is the four chamber (4C) view, FIG. 2E is the short axis (SHA) view, and FIG. 2F is the two chamber (2C) view.

Feature Engine

Feature engine 102 takes an input cardiac CT image 100 and computes various features such as: global binary features 104, statistical features 106, curvelet features 108, wavelet features 110, local binary features 112, and edge histogram features 114.

Group 1—Statistical Image Texture Features 106:

These include features calculated directly from the pixel intensity values in the image (non-limiting examples of such pixel intensity values include: minimum value, maximum value, mean, range, standard deviation, median, central moment, square sum, average top quartile, and average bottom quartile) and also those extracted from the co-occurrence matrices (entropy, energy, homogeneity). These features are calculated at different levels of granularity. Co-occurrence matrices of an image are histogram representations, each describing the co-occurrence of a pair of intensities at a certain distance (l) along a certain direction (θ). As an example, homogeneity is a measure of randomness in the image, which has low values for smooth images, and can be calculated from a given co-occurrence matrix, p, as follows:

$$H = \sum_i \sum_j \frac{p(i,j)}{1+|i-j|}$$

where i and j each go from 0 to 255 for an eight bit image. This equation returns larger values if similar intensities appear close to each other.

That is, both the global feature calculated over the entire image and the global features calculated over image partitions that divide the image into 2×2, 3×3, 5×5, 7×7 grids are included. The resulting features are concatenated to create a feature vector, per image.

Group 2—Curvelet Features 108:

Curvelet transform is a multiscale tool of image characterization with the ability to highlight image edges (see paper to Cao et al. titled "Multimedia Event Detection (MED), Multimedia Event Recounting (MER), and Semantic Indexing (SIN) Systems," NIST TRECVID Workshop, 2012, pp. 1-18). The version of curvelet transform used in this embodiment uses a Fourier polar pyramid. It incorporates ideas from both spatial pyramids and from the Curvelets feature transform. It constructs a spatial pyramid in Fourier space under the polar coordinate system, with 1, 2, 4 and partitions, and for each partition, it constructs a pyramid in the angular dimension, of partitions 1, 2, 4, 8, 16, and 32 segments. Due to the large size of the feature vector, only the global granularity for this group of features is used.

Group 3—Wavelet Features 110:

This group consists of 120 texture features obtained by discrete wavelet transform at each granularity. Haar wavelet was used. Haar discrete wavelet, at different scales, is shifted along the signal and for each position the spectrum is calculated as the convolution of the wavelet and the specific segment of the signal.

Group 4—Edge Histogram Features 114:

Edge histograms represent the frequency and the directionality of the brightness changes in the image. In the current embodiment, a histogram of edge directions is used with 64 bins resulting in 64 features, calculated per global, 2×2 and 3×3 granularity levels.

Group 5—Local Binary Pattern (LBP) Features 112:

LBPs are calculated by dividing the image into cells, and comparing the center pixel with neighboring pixels in the window (see, for example, paper to Ojala et al. titled "A Comparative Study of Texture Measures With Classification Based on Featured Distributions," Pattern Recognition, vol 29(1), 1996, pp. 51-59). A histogram is built that characterizes how many times, over the cell, the center pixel is larger or smaller than the neighbors. In the implementation used here, the histogram is built on different scales (1, ½, ¼ and ⅛ of the image), and a combined 59 dimensional histogram is produced. In this implementation, the LBP features are weighted by the inverse of the scale (see, for example, paper to Cao et al. titled "Multimedia Event Detection (MED), Multimedia Event Recounting (MER), and Semantic Indexing (SIN) Systems," NIST TRECVID Workshop, 2012, pp. 1-18).

Figure 3:
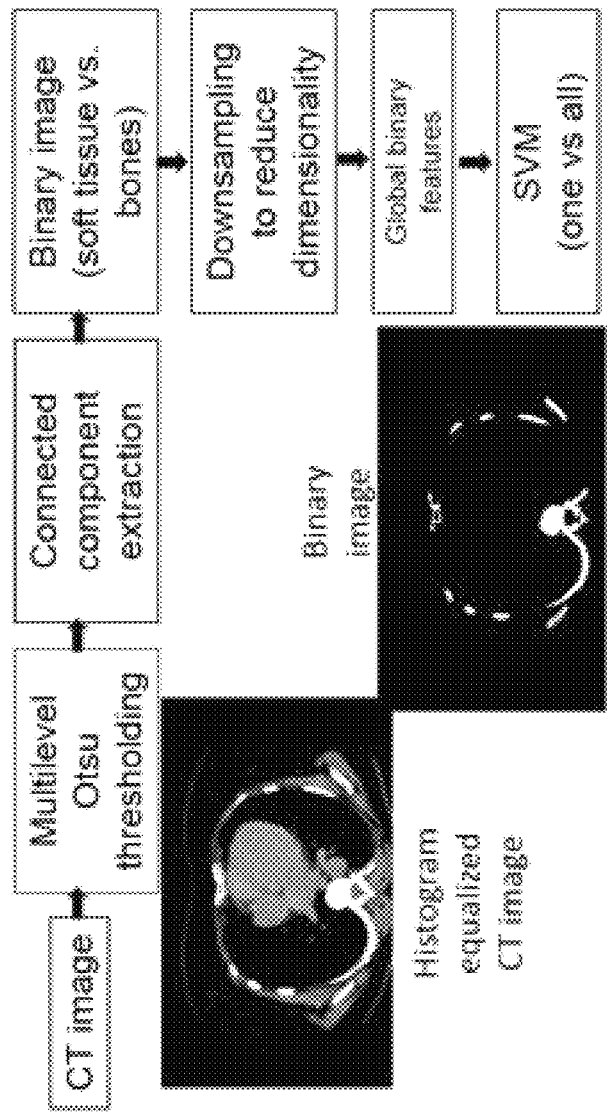
FIG. 3 depicts the present invention's GBP features calculation unit.
Figure 4:
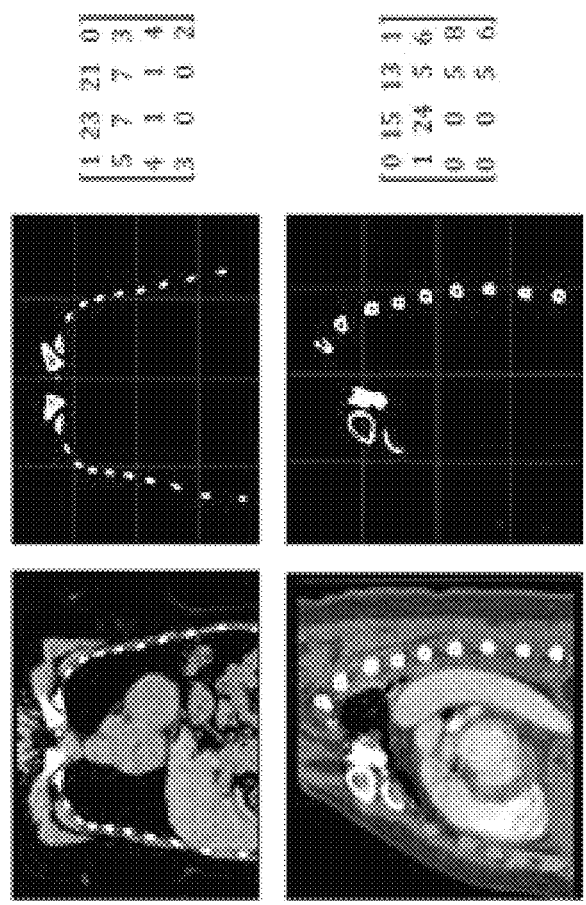
FIG. 4 depicts resulting sample binary images.

Group 6—Global Binary Pattern (GBP) Features 104:

This proposed set of features relies on the pattern of high intensity components of the anatomy of the chest, including the ribs and vertebrae. The images are first pre-processed with histogram equalization to a range routinely utilized by radiologists to maximize the contrast in cardiac chambers and vessels. Then multi-level Otsu thresholding, with four levels, is applied (see, for example, the paper to Liao et al. titled "A Fast Algorithm for Multilevel Thresholding," Journal of Information Science and Engineering, vol 17, 2001, pp. 51-59). Otsu thresholding calculates the optimal thresholds to minimize intra-level variance. The highest intensity level is then subjected to connected component clustering. The resulting connected components are then filtered based on the size of the area. FIG. 3 depicts the present invention's GBP features calculation unit. The image is first subjected to multilevel thresholding. Then, using a connected component extraction method, the connected level with the highest intensity is isolated. This is often the bones within a CT image without contrast enhancement. The rest of the components are combined with background as the dark background to obtain a binary image with a pixel value of 1 for bones and zero for the other pixels. This binary image is then down-sampled and vectorized to form a compact feature vector. An area size of 30 pixels is used in images of size 512×512. Samples of the resulting binary images are presented in FIG. 4. The binary image is then re-sized and down-sampled to obtain an m×m matrix, where m is chosen by experimentation from values of m=2, 4, 8, 16, 20. In FIG. 4, examples of this matrix m=4 are shown. The feature vector used for this method is the m²×1 vector generated by concatenating the columns of this matrix.

Classification

A support vector machine (SVM) classifier is used for each feature category. In FIG. 1, SVM 1 through SVM 6, labeled 118 through 128, have a one-to-one correspondence to the features calculation units 104 through 114. Given the large size of the feature vectors and the relatively small size of the dataset, the six different categories of features are not combined into a single vector. Instead, individual SVMs are used, which are then combined by voting. SVM training optimizes w and b to obtain the hyperplane $w^T\varnothing(x)+b$ where x is the feature vector and ø is the kernel function, to maximize the distance between the hyperplane and the closest samples (support vectors) in the two classes. SVM is by definition a binary classifier. In the present invention, three and six-class classification problems need to be solved. A one-versus-all approach is used to decide the label of each image for each feature group. In this approach, for an n class classification, n classifiers are trained, with each separating one of the viewpoint types from the rest of images. Each test sample is classified by the n classifiers, and "class likelihood" is calculated by 132 as described below for each of the n classifiers. The label with the largest class likelihood obtained from its corresponding one-versus-all classifier is chosen as the viewpoint suggested by the feature group for the test sample. In order to calculate the class likelihood, a method like the one noted within the paper to Platt titled "Probabilistic Outputs for Support Vector Machines and Comparisons to Regularized Likelihood Methods," Advances in Large Margin Classifiers, vol 10(3), 1999, pp. 61-74 is used. Given the SVM hyperplane obtained in training, the class likelihood ($L_c$) for class c for test sample $x_i$ is computed using a sigmoid function of form:

$$L_C = \frac{1}{1 + \exp(\alpha(W^T \phi(X_i) + b) + \beta)}$$

where α and β are calculated using maximum likelihood estimation on the training data. The following kernel functions were investigated: the linear kernel, radial basis function (RBF), and the polynomial kernel. There was no advantage in terms of accuracy when an RBF or polynomial kernel was used. The results obtained using the linear kernel where ø(X)=X is reported.

Voting 134:

The resulting six classifiers return six potentially different viewpoints for each image. In order to determine the final image label and maximize the accuracy, a majority voting scheme was used where the class label is determined as the most frequently returned label among the six classifiers. The result is reported as "correct" only if at least three classifiers return the correct label. A tie (3 to 3) vote can be decided based on the average class likelihoods.

Training and Testing Strategy 130:

A leave-one-sample out strategy was used for training and testing. Each sample serves as the hold-out once. For each of the classification problems, all feature specific classifiers are trained using all but the hold-out sample and the hold-out is used as the test sample. This is repeated until all samples are tested. In the six-class problem, six one-versus-all classifiers are trained per feature type which adds up to 36 SVMs to be trained for each leave-one-out step. In the three-class problem, there are 18 SVMs to be trained. Note that in all of these training and testing experiments, a linear SVM with similar parameters is employed. The SVM slack variable is set to C=1.

Results

Three-Class Classification of the Cardinal Planes:

Table 1 shows the results of the three-class classification of the axial, sagittal, and coronal images. For each feature group, the accuracy per class is listed along with the combined accuracy over the three classes. All the feature groups return overall accuracies over 90%. Curvelet, edge histograms, and GBP features approach or surpass 99% accuracy. The GBP matrix size is set to 4×4. Using the majority voting scheme, a consistently perfect classification is obtained.

TABLE 1

Accuracy of three-class classification-cardinal planes.

|  | Statistics | Curvelet | Wavelet | Edge | LBP | GBP |
| --- | --- | --- | --- | --- | --- | --- |
| Axial | 100% | 100% | 100% | 100% | 100% | 100% |
| Coronal | 85.7% | 100% | 100% | 100% | 92.9% | 100% |
| Sagittal | 92.9% | 100% | 92.9% | 100% | 92.9% | 96.4% |
| combined | 92.9% | 100% | 97.6% | 100% | 95.2% | 98.8% |
| voting |  |  | 100% |  |  |  |

Three-Class Classification of the Non-Cardinal Planes:

Table 2 reports the results of classification of 2C, 4C and SHA viewpoints. For this classification problem, the SVM trained on statistical texture features results in the most accurate classification with an overall accuracy of 100%, with the proposed simpler GBP being a close second at 96.4%. The GBP matrix size is set to 4×4. When the six classifiers are combined using voting, 83 out of 84 images are correctly classified resulting in an accuracy of 98.8%.

TABLE 2

Accuracy of three-class classification-non-cardinal planes.

|  | Statistics | Curvelet | Wavelet | Edge | LBP | GBP |
| --- | --- | --- | --- | --- | --- | --- |
| 2C | 100% | 92.9% | 92.9% | 92.9% | 85.7% | 96.4% |
| 4C | 100% | 100% | 100% | 100% | 100% | 96.4% |

TABLE 2-continued

Accuracy of three-class classification-non-cardinal planes.

|  | Statistics | Curvelet | Wavelet | Edge | LBP | GBP |
|---|---|---|---|---|---|---|
| SHA | 96.4% | 92.9% | 85.7% | 100% | 92.9% | 96.4% |
| combined | 99.4% | 95.2% | 92.9% | 97.6% | 92.8% | 96.4% |
| voting |  |  |  | 98.8% |  |  |

Six-Class Classification of all Images:

The accuracies in the six-class classification of the viewpoints are reported in Table 3. In this problem, the edge histogram and curvelet features return the highest accuracy and LBP and GBP are next, all with accuracies above 91%. The GBP matrix size is set to 16×16. The voting results in an accuracy of 99.4% where only one image is misclassified. This single case of misclassification is a sagittal image classified as a short axis image by five of the six feature group. Only the GBP SVM correctly classified this image. The most common misclassification in the feature specific SVM classifiers is the classification of two chamber images as coronal images. In all cases, however, this is rectified by voting. It is notable that all classifiers return 100% accuracy on the axial viewpoint which is the most commonly used view in cardiac CT imaging in clinical practice.

TABLE 3

Accuracy of six-class classification

|  | Statistics | Curvelet | Wavelet | Edge | LBP | GBP |
|---|---|---|---|---|---|---|
| Axial | 100% | 100% | 100% | 100% | 100% | 100% |
| Coronal | 78.6% | 100% | 100% | 100% | 85.7% | 100% |
| Sagittal | 78.6% | 92.9% | 64.3% | 100% | 92.9% | 92.9% |
| 2C | 85.7% | 85.7% | 92.9% | 100% | 85.7% | 85.7% |
| 4C | 100% | 100% | 100% | 100% | 100% | 85.7% |
| Short axis | 78.6% | 92.9% | 85.7% | 92.9% | 92.9% | 85.7% |
| combined | 85.7% | 95.2% | 90.5% | 98.8% | 91.6% | 91.6% |
| voting (three out of 6) |  |  |  | 99.4% |  |  |

In the area of medical imaging, big data is still elusive. A host of legal and ethical issues bar the free sharing of data. Gold standard labeling is also expensive. As a result, methods based on deep learning (see, for example, the paper to Krizhevsky et al. titled "Imagenet Classification with Deep Convolutional Neural Networks," Neural Information Processing Systems (NIPS) Proceedings, 2012, pp. 1-9) are difficult to tune for many medical imaging applications. It is shown that a curated set of features, including context-sensitive anatomic features, can provide a very accurate classification of cardiac CT viewpoints. In a recent work, IBM scientists have also developed a generalized framework for medical image classification and recognition which uses a large set of visual texture features extracted from image patches at various levels of granularity (see, for example, the paper to Codella et al. titled "Automated Medical Image Modality Recognition by Fusion of Visual and Text Information," MICCAI, vol 8674 of LNCS, 2014, pp. 487-495). These are used along with the ensembling method described in the paper to Caruana et al. titled "Ensemble Selection from Libraries of Models," Proceedings of the Twenty-first International Conference on Machine Learning, ICML '04, New York, N.Y., USA, ACM, 2004, pp. 18-26. Given the very large set of features and classifiers used in the paper to Codella et al. titled "Automated Medical Image Modality Recognition by Fusion of Visual and Text Information," MICCAI, vol 8674 of LNCS, 2014, pp. 487-495, a fair evaluation of this generalized solution for the specific problem of CT viewpoint recognition requires a larger dataset to avoid over-fitting.

An important feature of our current work is the use of GBP that constitutes a set of context-sensitive features as opposed to the general purpose features used in the paper to Codella et al. titled "Automated Medical Image Modality Recognition by Fusion of Visual and Text Information," MICCAI, vol 8674 of LNCS, 2014, pp. 487-495, and elsewhere. It should be noted that in contrast-enhanced CT, depending on the time of imaging, high intensities could appear within heart chambers as well. Our dataset was from contrast-enhanced CT and this issue is likely to have contributed to some of the errors in GBP classification. More sophisticated methods of segmenting the bones, including atlas-based approaches, could provide a more accurate binary image. Nevertheless, despite the simplicity of the binarization approach, a highly effective set of features were obtained through this method which ranks among the top three groups of features in terms of accuracy in all experiments. The GBP features calculated with this approach are also the least computationally expensive group of features.

The specific machine learning framework developed here is based on linear SVMs. While SVM is inherently binary, it is still shown that a multiclass solution with class likelihood estimation and voting may be effectively built. An alternative solution is using random forests. The need for nearly perfect classification of the viewpoints, as the first step in the deployment of a cognitive assistant system for cardiologists, requires a very robust solution. Therefore, a system based on several classifiers and voting is needed. The top contributors to the classification accuracy in the six way problem were edge, curvelet, GBP and LBP features.

In order to build a fully automatic cognitive assistant, the classification problem needs to be expanded to include not only other viewpoints such as three or five chamber views, but also the slice level. Our future work will address these more complicated problems with GBPs and classical features.

Figure 5:
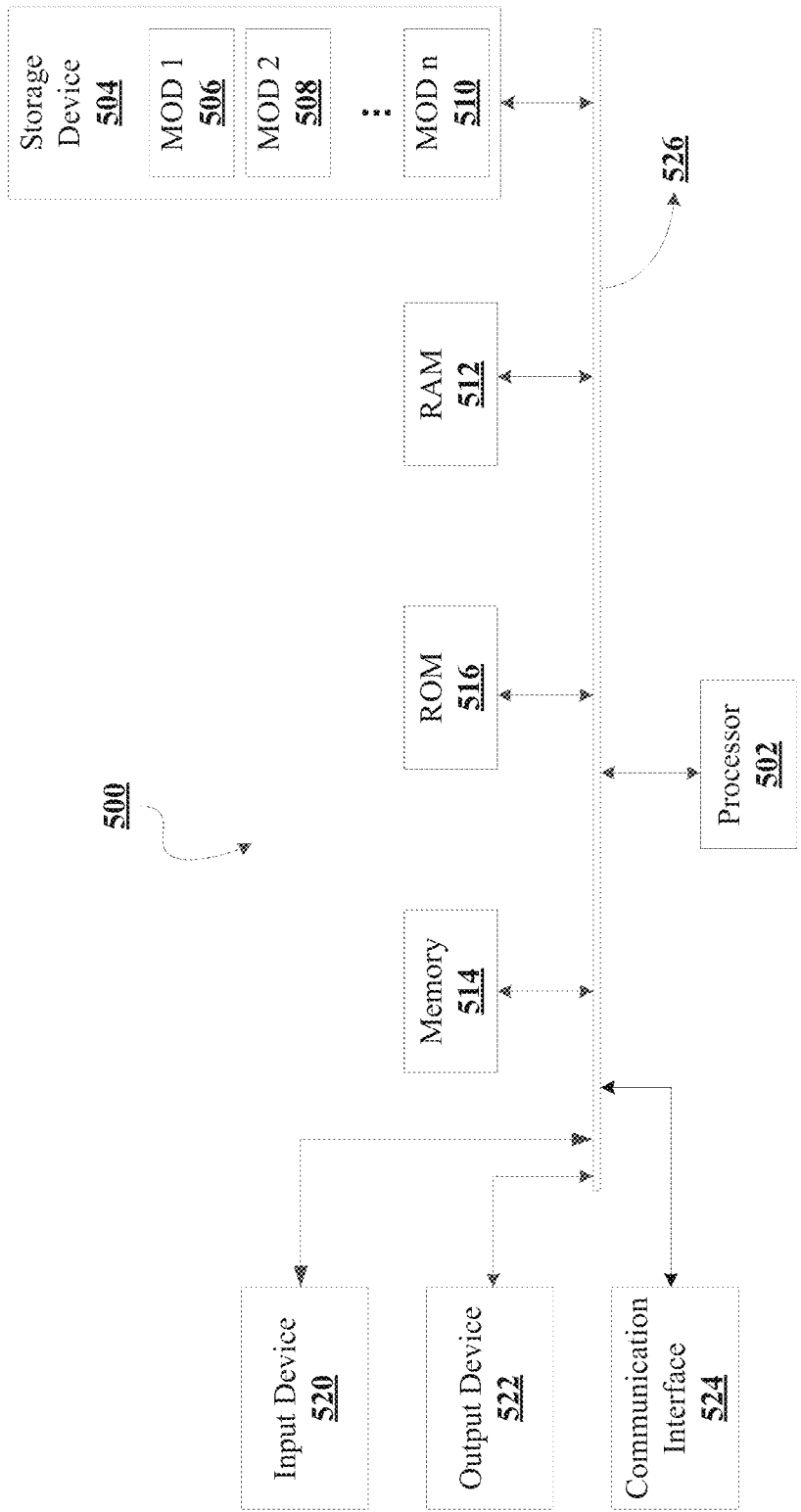
FIG. 5 depicts a system for implementing the present invention's methods.

The logical operations of the various embodiments are implemented as: (1) a sequence of computer implemented steps, operations, or procedures running on a programmable circuit within a general use computer, (2) a sequence of computer implemented steps, operations, or procedures running on a specific-use programmable circuit; and/or (3) interconnected machine modules or program engines within the programmable circuits. The system 500 shown in FIG. 5 can practice all or part of the recited methods, can be a part of the recited systems, and/or can operate according to instructions in the recited non-transitory computer-readable storage media. With reference to FIG. 5, an exemplary system includes a general-purpose computing device 500, including a processing unit (e.g., CPU) 502 and a system bus 526 that couples various system components including the system memory such as read only memory (ROM) 516 and random access memory (RAM) 512 to the processing unit 502. Other system memory 514 may be available for use as well. It can be appreciated that the invention may operate on a computing device with more than one processing unit 502 or on a group or cluster of computing devices networked together to provide greater processing capability. A processing unit 520 can include a general purpose CPU controlled by software as well as a special-purpose processor.

The computing device 500 further includes storage devices such as a storage device 504 such as, but not limited to, a magnetic disk drive, an optical disk drive, tape drive or the like. The storage device 504 may be connected to the system bus 526 by a drive interface. The drives and the associated computer readable media provide nonvolatile storage of computer readable instructions, data structures, program modules and other data for the computing device 500. In one aspect, a hardware module that performs a particular function includes the software component stored in a tangible computer-readable medium in connection with the necessary hardware components, such as the CPU, bus, display, and so forth, to carry out the function. The basic components are known to those of skill in the art and appropriate variations are contemplated depending on the type of device, such as whether the device is a small, handheld computing device, a desktop computer, or a computer server.

Although the exemplary environment described herein employs the hard disk, it should be appreciated by those skilled in the art that other types of computer readable media which can store data that are accessible by a computer, such as magnetic cassettes, flash memory cards, digital versatile disks, cartridges, random access memories (RAMs), read only memory (ROM), a cable or wireless signal containing a bit stream and the like, may also be used in the exemplary operating environment.

Logical operations can be implemented as modules configured to control the processor 502 to perform particular functions according to the programming of the module. FIG. 5 also illustrates three modules MOD 1 506, MOD 2 508 and MOD 3 510, which are modules controlling the processor 502 to perform particular steps or a series of steps. These modules may be stored on the storage device 504 and loaded into RAM 512 or memory 514 at runtime or may be stored as would be known in the art in other computer-readable memory locations.

Modules MOD 1 506, MOD 2 508 and MOD 3 510 may, for example, be modules controlling the processor 502 to perform the following steps to implement a method for computed tomography (CT) viewpoint recognition in CT images: preprocessing the CT images with histogram equalization to maximize contrast in one or more pre-determined regions; applying Otsu thresholding to the preprocessed CT images and extracting connected components; forming a feature vector based on the extracted connected components; applying a plurality of support vector machine (SVM) classifiers, one for the feature vector formed from extracted connected components and one for each calculated conventional feature; and picking a class label for each of the CT images based on a majority voting scheme determining the most frequently returned label among the SVM classifiers.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

CONCLUSION

A system and method has been shown in the above embodiments for the effective implementation of viewpoint recognition in computer tomography images. While various preferred embodiments have been shown and described, it will be understood that there is no intent to limit the invention by such disclosure, but rather, it is intended to cover all modifications falling within the spirit and scope of the invention, as defined in the appended claims. For example, the present invention should not be limited by software/program, computing environment, or specific computing hardware.

The invention claimed is:

1. A system for computed tomography (CT) viewpoint recognition in CT images comprising:
    a feature engine comprising a global binary pattern feature calculation unit and at least one image feature calculation unit, said global binary pattern feature calculation unit: (i) preprocessing said CT images with histogram equalization to maximize contrast in one or more pre-determined regions, (ii) extracting connected components from said preprocessed CT images, and (iii) forming a feature vector based on said extracted connected components;
    a cognitive engine comprising: (i) a plurality of classifiers, one for each of said global binary calculation unit, and (ii) at least one image feature calculation unit; and
    a voting unit picking a class label for each of the CT images based on a majority voting scheme determining the most frequently returned label among said classifiers.

2. The system of claim 1, wherein said CT images are cardiac CT images.

3. The system of claim 2, wherein said class label is any of the following: short axis view (SHA), two chamber view (2C), and four chamber view (4C).

4. The system of claim 1, wherein said connected components are extracted by applying Otsu thresholding.

5. The system of claim 4, wherein said Otsu thresholding is performed with four levels.

6. The system of claim 5, wherein said Otsu thresholding step comprises: calculating optimal thresholds to minimize intra level variance, applying component clustering to a highest intensity level, and filtering and outputting connected components as said extracted connected components.

7. The system of claim 1, wherein said classifiers are support vector machine (SVM) classifiers.

8. A system for computed tomography (CT) viewpoint recognition in CT images comprising:
    a feature engine comprising:
        one or more image feature calculation units selected from a group consisting of: a statistical image texture feature calculation unit, a curvelet feature calculation unit, a wavelet feature calculation unit, an edge histogram features calculation unit, and a local binary pattern (LBP) features calculation unit; and
        a global binary pattern feature calculation unit: (i) preprocessing said CT images with histogram equalization to maximize contrast in one or more pre-determined regions, (ii) extracting connected components from said preprocessed CT images, and (iii) forming a feature vector based on said extracted connected components;
    a cognitive engine comprising a plurality of classifiers, (i) one for each of said global binary calculation unit, and (ii) one for each of said image feature calculation units; and
    a voting unit picking a class label for each of the CT images based on a majority voting scheme determining the most frequently returned label among said classifiers.

9. The system of claim 8, wherein said CT images are cardiac CT images.

10. The system of claim 9, wherein said class label is any of the following: short axis view (SHA), two chamber view (2C), and four chamber view (4C).

11. The system of claim 8, wherein said connected components are extracted by applying Otsu thresholding.

12. The system of claim 11, wherein said Otsu thresholding is performed with four levels.

13. The system of claim 12, wherein said Otsu thresholding step comprises: calculating optimal thresholds to minimize intra level variance, applying component clustering to a highest intensity level, and filtering and outputting connected components as said extracted connected components.

14. The system of claim 8, wherein said classifiers are support vector machine (SVM) classifiers.

15. A method for computed tomography (CT) viewpoint recognition in CT images comprising:
    preprocessing said CT images with histogram equalization to maximize contrast in one or more pre-determined regions;
    extracting connected components from said preprocessed CT images;
    forming a feature vector based on said extracted connected components;
    applying a plurality of classifiers, (i) one for said feature vector formed from extracted connected components, and (ii) at least one additional classifier for a calculated image feature; and
    picking a class label for each of the CT images based on a majority voting scheme determining the most frequently returned label among said classifiers.

16. The method of claim 15, wherein said CT images are cardiac CT images.

17. The method of claim 16, wherein said class label is any of the following: short axis view (SHA), two chamber view (2C), and four chamber view (4C).

18. The method of claim 15, wherein said connected components are extracted by applying Otsu thresholding.

19. The method of claim 18, wherein said Otsu thresholding is performed with four levels and said Otsu thresholding step comprises: calculating optimal thresholds to minimize intra level variance, applying component clustering to a highest intensity level, and filtering and outputting connected components as said extracted connected components.

20. The method of claim 15, wherein said classifiers are support vector machine (SVM) classifiers.

21. A method for use with a 3-D computed tomography (CT) image of anatomy relevant to a medical condition, the method comprising:
    generating a binary image of the CT image, said binary image delineating bone from soft tissue;
    analyzing said binary image with a machine learning component to train a classifier within said machine learning component and generating a taxonomy related to anatomical viewpoints of the CT image;

ranking a plurality of 2-D slices of the CT image based on said generated taxonomy; and selecting a 2-D slice among said plurality of 2-D slices that is most relevant to the medical condition based on said ranking.

22. The method of claim 21, wherein said CT image is of a human chest, including the heart, and the viewpoints correspond to portions of the heart.

23. The method of claim 21, wherein said machine learning component includes support vector machines (SVMs).

24. The method of claim 23, wherein said SVMs vote to determine said selected 2-D slice among said plurality of 2-D slices.

\* \* \* \* \*